(12) United States Patent
Flickinger et al.

(10) Patent No.: US 8,790,403 B2
(45) Date of Patent: Jul. 29, 2014

(54) MONORAIL SYSTEM

(75) Inventors: Eric Flickinger, Atlanta, GA (US); Tom Smithweck, Powder Springs, GA (US)

(73) Assignee: K2M, Inc., Leesburg, CA (US)

( * ) Notice: Subject to any disclaimer, the term of this patent is extended or adjusted under 35 U.S.C. 154(b) by 514 days.

(21) Appl. No.: 12/614,499

(22) Filed: Nov. 9, 2009

(65) Prior Publication Data

US 2010/0121388 A1    May 13, 2010

Related U.S. Application Data

(63) Continuation-in-part of application No. 11/407,585, filed on Apr. 20, 2006, now Pat. No. 7,615,079.

(51) Int. Cl.
| | |
|---|---|
| A61F 2/44 | (2006.01) |
| A61B 17/02 | (2006.01) |
| A61B 17/16 | (2006.01) |
| A61F 2/46 | (2006.01) |
| A61F 2/30 | (2006.01) |
| A61B 17/17 | (2006.01) |

(52) U.S. Cl.
CPC ....... *A61B 17/025* (2013.01); *A61F 2250/0097* (2013.01); *A61B 17/1604* (2013.01); *A61F 2002/4681* (2013.01); *A61F 2/447* (2013.01); *A61F 2/4611* (2013.01); *A61F 2250/0063* (2013.01); *A61F 2002/30611* (2013.01); *A61F 2002/4629* (2013.01); *A61B 2017/0256* (2013.01); *A61F 2002/30617* (2013.01); *A61F 2/446* (2013.01); *A61F 2002/30841* (2013.01); *A61F 2002/4475* (2013.01); *A61F 17/1671* (2013.01); *A61F 2002/448* (2013.01); *A61B 17/1757* (2013.01); *A61F 2002/4627* (2013.01); *A61F 2002/30785* (2013.01); *A61B 17/1735* (2013.01)
USPC ........................................................ 623/17.11

(58) Field of Classification Search
USPC .................... 606/90, 99, 104, 86 A, 86 R; 623/17.11–17.16
See application file for complete search history.

(56) References Cited

U.S. PATENT DOCUMENTS

| | | | | |
|---|---|---|---|---|
| 5,015,247 A | * | 5/1991 | Michelson | 606/247 |
| 5,571,109 A | * | 11/1996 | Bertagnoli | 606/86 A |
| 5,713,906 A | | 2/1998 | Grothues-Spork et al. | |
| 5,885,299 A | * | 3/1999 | Winslow et al. | 606/99 |
| 5,968,098 A | * | 10/1999 | Winslow | 623/17.11 |
| 6,110,177 A | | 8/2000 | Ebner et al. | |
| 6,156,040 A | * | 12/2000 | Yonemura et al. | 606/99 |
| 6,267,763 B1 | | 7/2001 | Castro | |

(Continued)

FOREIGN PATENT DOCUMENTS

| | | |
|---|---|---|
| DE | 10035182 | 2/2002 |
| WO | WO-0042898 | 7/2000 |
| WO | WO-02062235 | 8/2002 |
| WO | WO-2007074295 | 7/2007 |

*Primary Examiner* — Mary Hoffman
*Assistant Examiner* — Michelle C Eckman
(74) *Attorney, Agent, or Firm* — Carter, DeLuca, Farrell & Schmidt

(57) ABSTRACT

Systems for improved methods of performing a spinal fusion procedure that include a monorail instrument having a sliding platform for additional instrumentation to allow controlled delivery of various instruments for disc preparation and implant insertion in order to protect the medial neural structures of the spine. The monorail instrument engages other instruments, including various instruments utilized to prepare the disc space as well as spinal fusion implants, for guided and controlled insertion into the disc space. The monorail instrument may be a distractor, and may include flutes for preparation of the disc space.

20 Claims, 19 Drawing Sheets

(56) References Cited

U.S. PATENT DOCUMENTS

| | | | |
|---|---|---|---|
| 6,368,325 B1* | 4/2002 | McKinley et al. | 606/99 |
| 6,478,800 B1 | 11/2002 | Fraser et al. | |
| 6,491,695 B1 | 12/2002 | Roggenbuck | |
| 6,500,180 B1 | 12/2002 | Foley et al. | |
| 6,540,753 B2* | 4/2003 | Cohen | 606/99 |
| 6,554,836 B2* | 4/2003 | Michelson | 606/86 R |
| 6,755,841 B2* | 6/2004 | Fraser et al. | 606/99 |
| 6,824,565 B2 | 11/2004 | Muhanna et al. | |
| 6,855,148 B2 | 2/2005 | Foley et al. | |
| 6,887,248 B2 | 5/2005 | McKinley et al. | |
| 6,929,606 B2 | 8/2005 | Ritland | |
| 6,936,070 B1 | 8/2005 | Muhanna | |
| 6,951,538 B2 | 10/2005 | Ritland | |
| 7,267,690 B2 | 9/2007 | Felt | |
| 7,481,812 B2* | 1/2009 | Frey et al. | 606/85 |
| 7,615,079 B2 | 11/2009 | Flickinger et al. | |
| 2002/0055745 A1* | 5/2002 | McKinley et al. | 606/99 |
| 2003/0032966 A1* | 2/2003 | Foley et al. | 606/105 |
| 2003/0130662 A1* | 7/2003 | Michelson | 606/79 |
| 2003/0135277 A1* | 7/2003 | Bryan et al. | 623/17.12 |
| 2004/0073214 A1 | 4/2004 | Mehdizadeh | |
| 2004/0093083 A1 | 5/2004 | Branch | |
| 2004/0176775 A1* | 9/2004 | Burkus et al. | 606/90 |
| 2004/0267276 A1 | 12/2004 | Camino | |
| 2005/0154396 A1* | 7/2005 | Foley et al. | 606/90 |
| 2005/0216088 A1 | 9/2005 | McKinley et al. | |
| 2005/0240273 A1* | 10/2005 | Khandkar et al. | 623/17.15 |
| 2005/0251146 A1* | 11/2005 | Martz et al. | 606/84 |
| 2006/0036261 A1* | 2/2006 | McDonnell | 606/99 |
| 2006/0217731 A1* | 9/2006 | Gil et al. | 606/86 |
| 2007/0123903 A1* | 5/2007 | Raymond et al. | 606/99 |
| 2007/0270873 A1 | 11/2007 | Flickinger et al. | |
| 2007/0276406 A1* | 11/2007 | Mahoney et al. | 606/106 |
| 2008/0051902 A1* | 2/2008 | Dwyer | 623/17.16 |
| 2008/0140206 A1 | 6/2008 | Felt | |
| 2008/0269756 A1* | 10/2008 | Tomko et al. | 606/87 |
| 2008/0312741 A1* | 12/2008 | Lee et al. | 623/17.11 |
| 2010/0076557 A1* | 3/2010 | Miller | 623/17.11 |

* cited by examiner

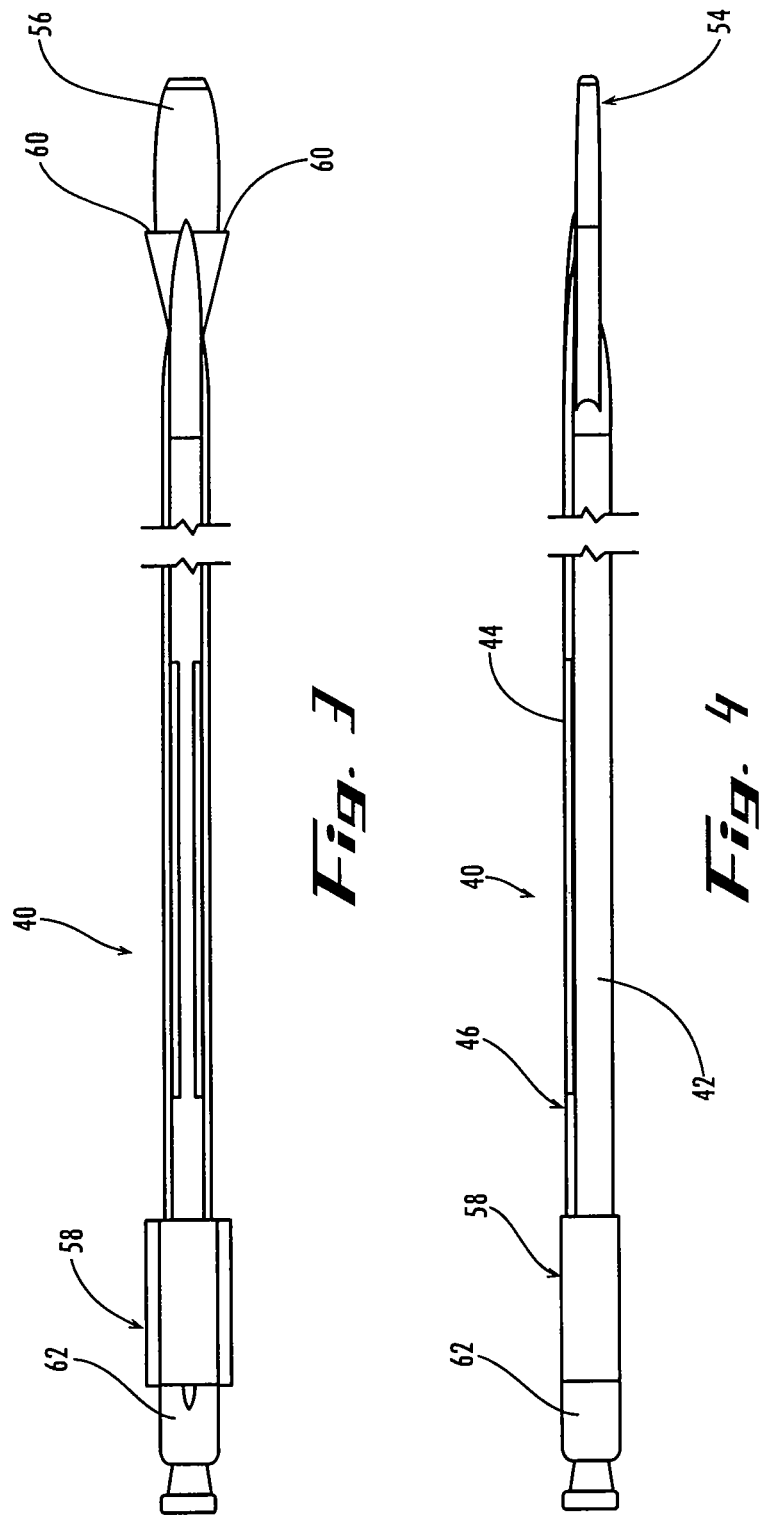

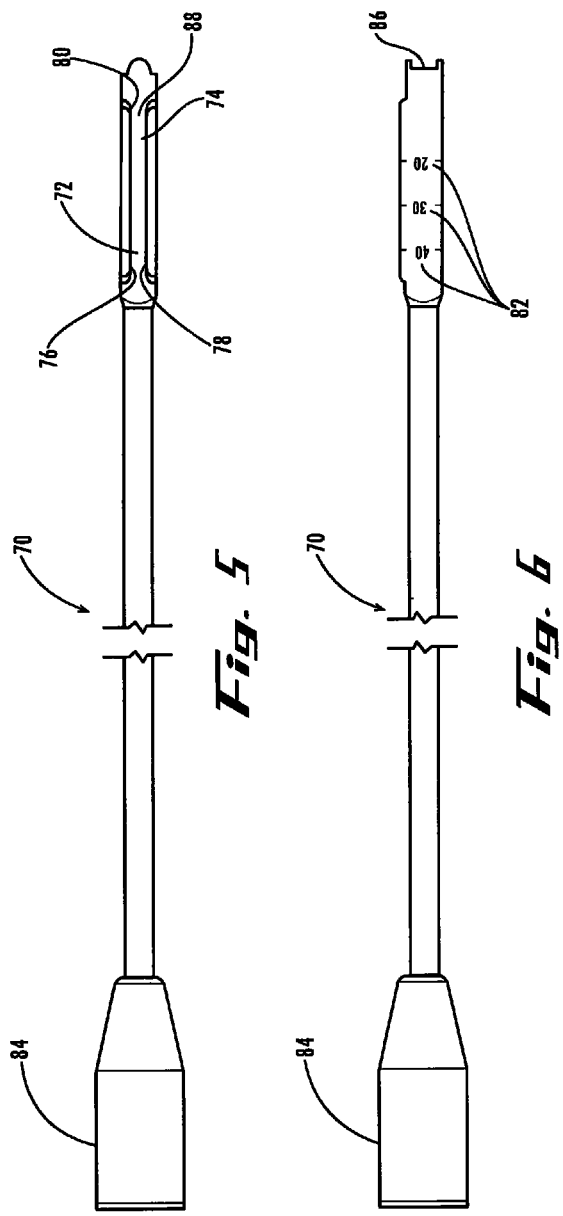

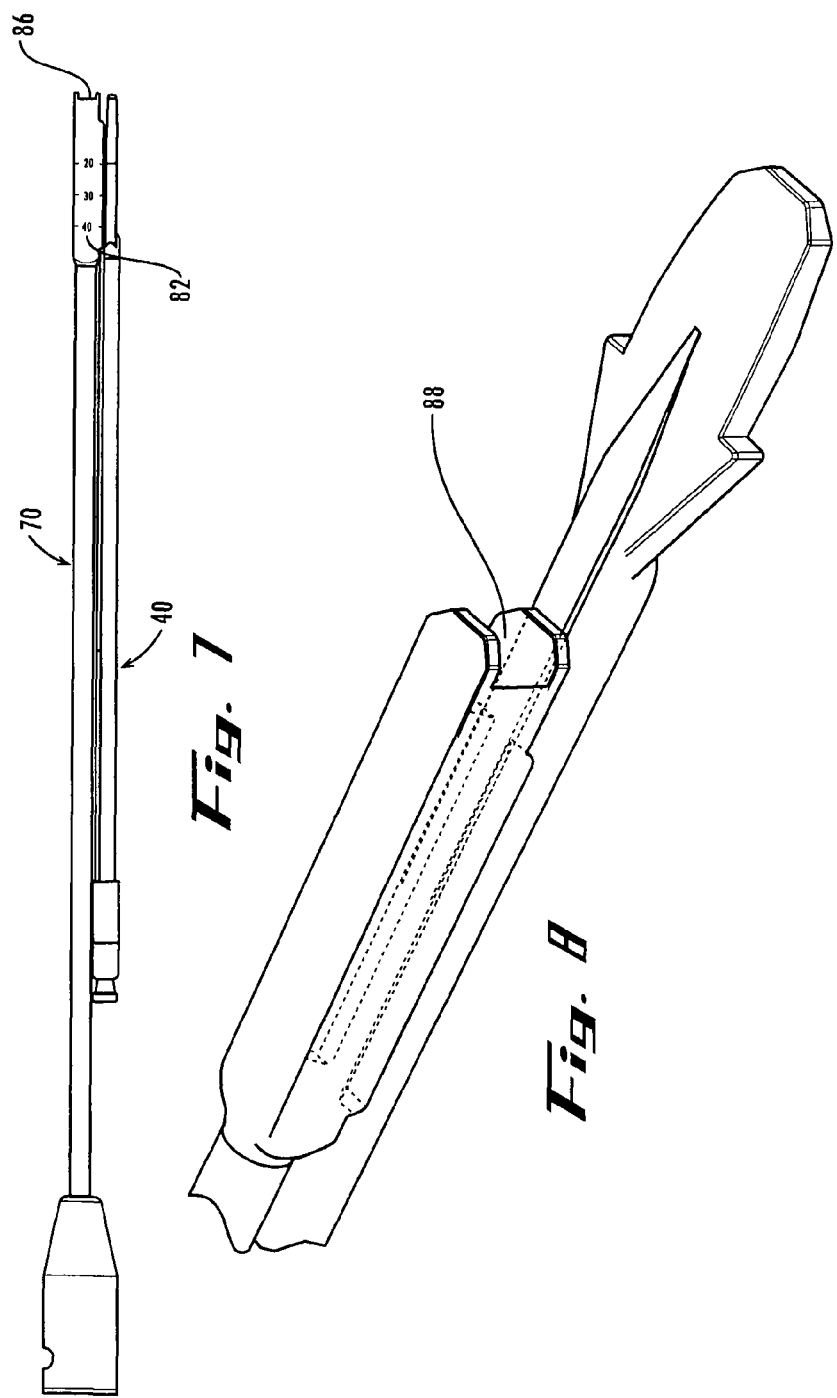

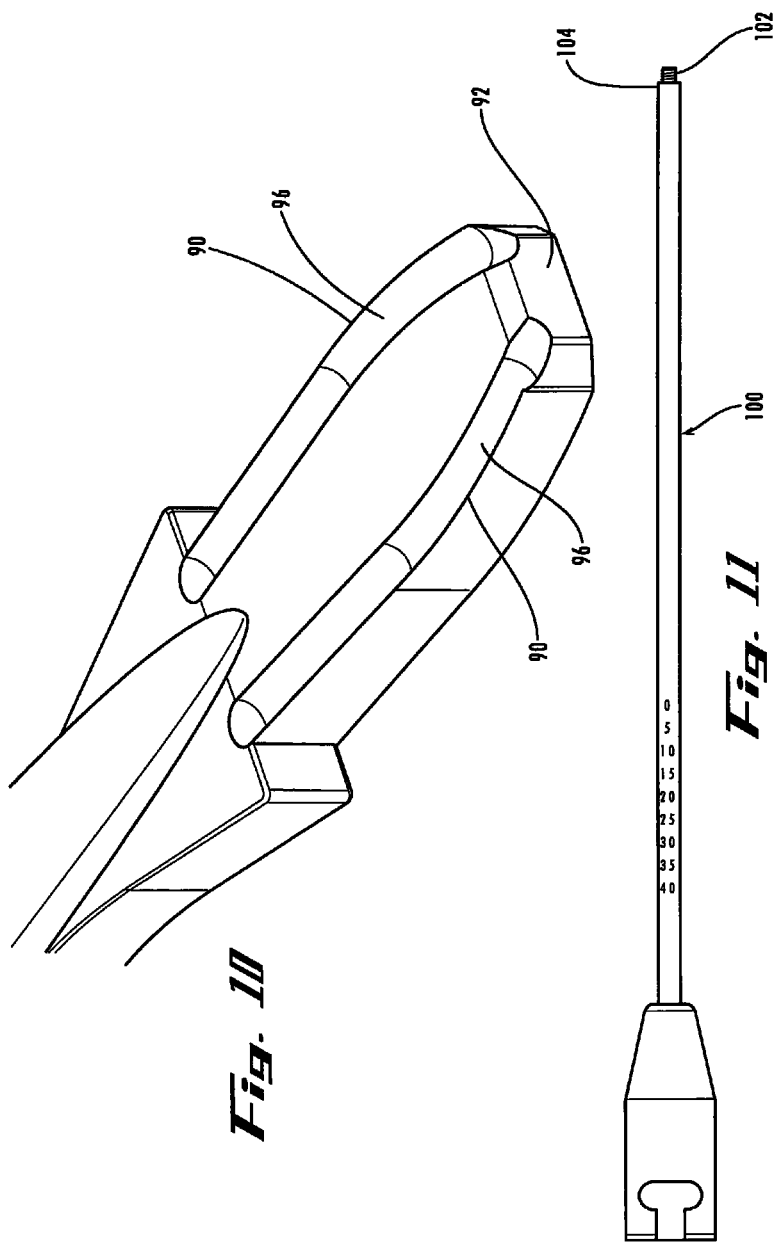

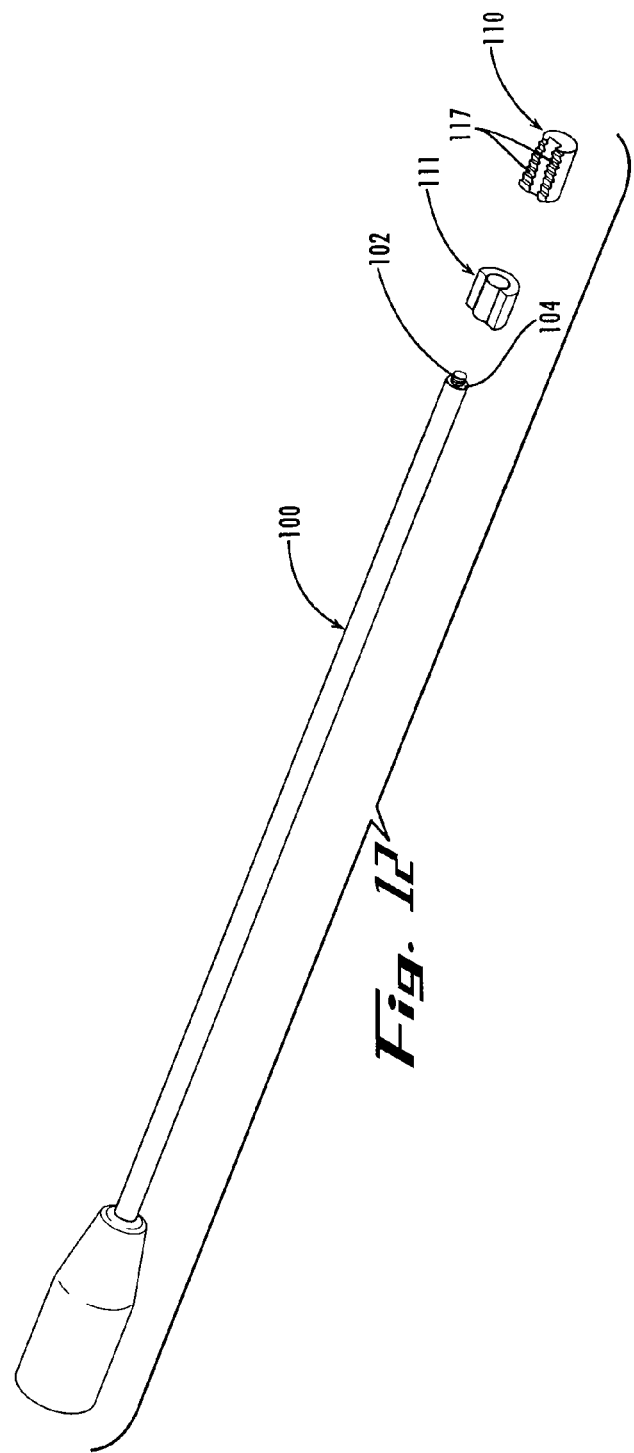

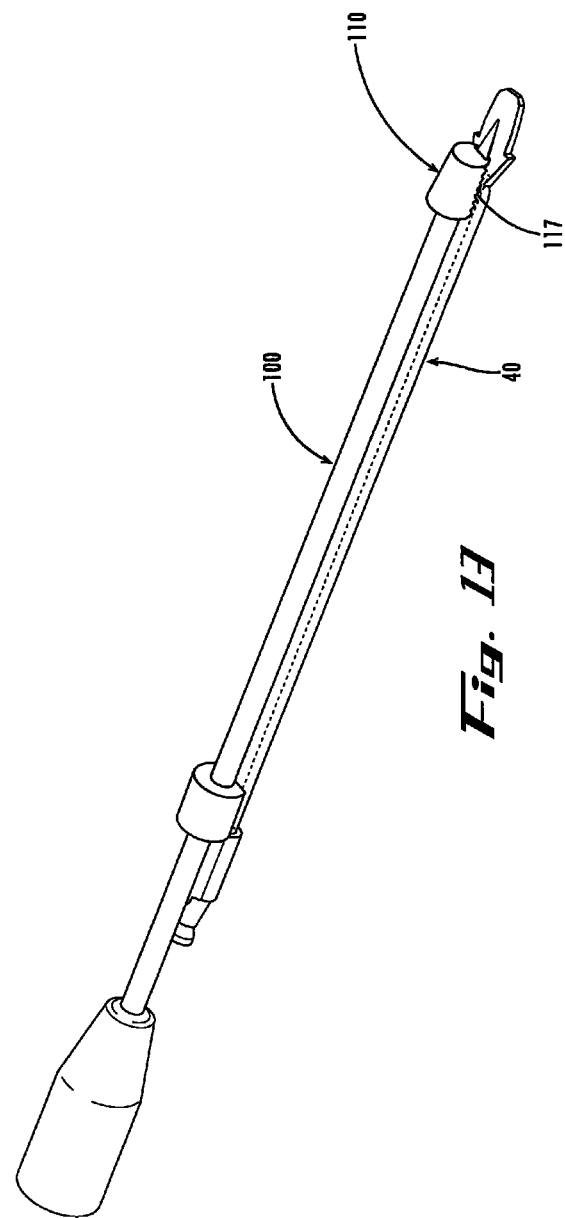

MONORAIL SYSTEM

RELATED APPLICATIONS

This application is a continuation-in-part of pending U.S. patent application Ser. No. 11/407,585, filed on Apr. 20, 2006, the entire contents of which are hereby incorporated by reference.

FIELD OF THE INVENTION

This invention relates generally to spinal surgery and, in particular, to a system for safely and effectively delivering instruments and implants to the spine during spinal surgery

BACKGROUND

The spinal column is a flexible column formed from a linear series of vertebral bones separated by intervertebral discs. These discs reduce friction between adjacent vertebrae and absorb compression forces applied to the spinal column. A vertebra includes an anterior body and a posterior arch that surrounds the spinal cord. Spinal nerves extend from each side of the spinal cord and exit the column at the vertebral foramen, which is formed by the posterior arch. Articular processes, including the superior articular process and the inferior articular process, are small flat projections on the surfaces of the arches.

There are four facet joints associated with each vertebrae, and these joints interlock with adjacent vertebrae. In this manner, facets on the opposing processes determine the range and direction of movement between adjacent vertebrae, hence the flexibility of the spinal column. The facet joints maintain spinal stability, protect the disc from excessive stress, and assist the discs in allowing motion and controlling shear forces. These joints are vulnerable to degenerative spinal disorders.

Degenerative disc disease is typically caused by a loss of disc space height, leading to a narrowing of the neural foramen and subsequent neural compression, and causing back and radicular pain. Instability of the posterior elements can lead to a condition known as spondylolisthesis, in which a vertebral body slips forward in relation to an adjacent vertebrae. This movement of the vertebral body narrows the foramen and results in painful pressure on the nerve roots.

Degenerative disc disease may often be resolved through a spinal fusion procedure using an interbody implant (one which is implanted between the bodies of two adjacent vertebrae). Such interbody implants may be formed from titanium, carbon fiber, allograft, or other suitable material including, but not limited to, biocompatible materials such as PEEK™, available from Invibio®. Implantation of a substitute graft is designed to reestablish normal disc height, provide immediate stability to the motion segment, and provide a matrix for fusion. When the implant grows into the existing bone, the fusion becomes solid and movement is eliminated at that level. A fusion procedure may also involve the surgical implantation of hardware, such as plates, screws or cages.

In order to fuse and thereby stabilize the motion segment, the disc space must be prepared prior to insertion of the interbody implantation device. Soft tissue, such as disc material and cartilage, and other such tissue, is cleaned off the vertebral endplates so that intimate bony contact is obtained between the graft, implant and host tissue. The preparation of the disc space can be achieved with rectangular, anatomical or rotary type scrapers, curettes, rongeurs, drills, rasps and/or chisels. In preparing the disc space, it is important not to remove too much of the endplate in order to maintain structural integrity so that the interbody implant does not telescope into the vertebral body when normal axial loads are applied.

The interbody space for lumbar surgery has always challenged surgeons when trying to access the space to achieve arthrodesis. Posterior Lumbar Interbody Fusion (PLIF) is one surgical fusion technique used to treat degenerative lumbar disc disease. Proper distraction during a PLIF procedure must be achieved in order to gain compression of the implant through ligamentous taxis. Proper distraction allows natural compression across the disc space via the annulus and other posterior elements as well as the anterior longitudinal ligament. This compression delivered to the implant helps stabilize the implant, which prevents expulsion, and keeps the grafting material under stress, thus promoting faster fusion and bone healing. Existing techniques for reaching the interbody space from a posterior approach include the use of Cloward dowels, threaded cages, impacted cages and impacted allografts. All of these techniques have limitations as well as complications, as they involve extensive nerve root retraction as well as destabilization through destruction of bony and ligamentous structures.

Initially, Anterior Lumbar Interbody Fusion (ALIF) was utilized to avoid the posterior structures of the spine. However, the anterior approach (from the patient's abdomen) to the disc space also presents challenges and limitations because of the potential of vascular injuries. In addition, not all of the lumbar spinal segments can be reached from an anterior incision without potential complications. Retroperitoneal approaches have helped eliminate some of the vascular injuries, but the potential still exists. It is known in the art that revision surgery is greatly complicated by scarring from the initial procedure, especially in the case of total disc replacement (TDR).

Because of the challenges with the PLIF and ALIF procedures, surgeons have adopted other approaches to the posterior spine. Transforaminal Lumbar Interbody Fusion (TLIF), also referred to as an extended PLIF, has emerged as another means of accessing the interbody space. TLIF involves the removal of one facet joint, usually on the more diseased or symptomatic side of the spine. PLIF is usually performed bilaterally, removing a portion (if not all) of each of the facet joints. Removal of the entire facet joint improves visualization into the disc space, allowing removal of more disc material and insertion of a larger implant. The transforaminal approach (TLIF) limits the nerve root injuries associated with the PLIF procedure because the disc space and spinal canal is approached from one side of the intervertebral space. This allows the surgeon to operate with minimal stretching of nerve roots. Various banana-shaped implants have been designed to be impacted across the disc space to achieve arthrodesis. Although longer, straight implants have been placed across the disc space with some success, the lordotic angle of the spine is harder to properly match with these straight implants. The banana-shaped implant helps maintain proper lordosis when it is placed in the anterior third of the disc space. Despite the benefits of the TLIF procedure, TLIF still suffers from limitations involving bony and soft tissue destruction and bilateral pathology.

Another approach to the lumbar spine that has gained some popularity is the far lateral approach, which involves approaching the spine from the side of the patient thru the psoas muscle. This lateral approach was devised in an attempt to avoid the complications associated with the posterior and anterior approaches to the spine. This technique provides an additional way to access the interbody space for fusion as well as for motion preservation procedures. While there is potential for nerve injury (though limited by using nerve monitoring equipment) and psoas muscle irritation, the muscles are spared through dilation instruments. Once the disc space is exposed, complete discectomy can be performed to prepare the fusion bed. Since the far lateral procedure avoids anterior entry, vascular structures are not compromised or scarred, eliminating possible complications in following salvage procedures.

Existing methods of introducing interbody implants into the disc space, the freehand method and the controlled method, include disadvantages. First, existing "freehand" techniques, in which an implant is inserted into the disc space without controlled access and impacted into proper position, present dangers to delicate neural structures. Each time an instrument is introduced or removed from the surgical site, there is a chance that delicate structures, such as the spinal cord or nerve roots, could be compromised, potentially causing severe injury. Additionally, maintaining constant distraction is a challenge, as instruments are passed by the neural structures freehand. Moreover, if a distractor is placed in the contralateral side of implantation, it can be cumbersome and it does not always address the distraction needs of the operative side.

In existing "controlled" procedures (e.g., threaded cages), the instruments used to provide protected access to the disc space often occupy an excessive amount of the disc space. As a result, an implant smaller than that which the disc space is capable of accepting must be used. This smaller implant does not restore proper disc space height, and therefore the stability of the fusion is compromised. Furthermore, these instruments require much bonier resection in order to be placed correctly, thus further destabilizing the spine.

In another existing controlled procedure, a series of instruments slide through a channel of a wide profile distractor. This design limits visualization and neural retraction. In addition, the design introduces a significant amount of lateralization to the placement of the implants for PLIF procedures: the implants are spaced farther apart from one another and must be implanted with a significant amount of space between them. Further, this delivery design has poor anatomical fit, as it creates a dead space between the external wall of the retractor and the load bearing surface of the implant.

The instruments used in existing procedures include design limitations that fail to address the challenges of the neural anatomy or require numerous instruments and steps that add significant time to the surgical procedure. Delivery of an interbody device requires a large amount of bone resection and neural retraction. Removal of the lamina and facet joint, which may be necessary in order to insert the implant, can potentially destabilize the motion segment. In addition, there is increased surgical time due to the more extensive bone removal and disc preparation. Destabilization of the motion segment can interfere with compression of the interbody device, especially in a "stand alone" situation in which additional hardware is not utilized. Therefore, it is necessary to balance the need to deliver an appropriately sized interbody device (to restore the appropriate disc height) without destabilizing the segment (so the necessary compression can occur).

SUMMARY

Systems of the present invention provide improved methods of performing spinal fusion and total disc replacement procedures. A monorail instrument according to this invention protects the medial neural structures, provides a sliding monorail platform for additional instrumentation and allows controlled delivery of various instruments for disc preparation and implant insertion. The monorail system of this invention may be adapted for use with each of the PLIF, TLIF, ALIF and far lateral or extreme lateral procedures.

One instrument according to certain exemplary embodiments of the invention includes a distractor instrument with a monorail on a lateral side that engages and secures an implant device as well as various surgical instruments used to prepare the disc space. The surgical instruments, as well as implants, may be designed with a recessed channel corresponding to the monorail, so that the instruments are joined to the monorail instrument for guided and controlled insertion into the disc space. The distractor instrument may include flutes or other cutting means for preparation of the disc space.

In use, two monorail distractors according to certain exemplary embodiments of the invention may be inserted into the disc space from opposite direct lateral incisions. In this embodiment, two distractors are inserted into the same surgical site in order to prepare and reconstruct the disc space. The preparation and reconstruction of the disc space through the use of two distractors is useful whether a fusion device or a motion preserving device is used. The monorails are placed on either sides of the disc space to maintain stability and distraction while delivering instruments and implants to the disc space. Two distractors are also used for the purpose of restoring lordosis or maintaining proper lordosis. One or more monorail instruments may also be inserted into the disc space from a posterior, anterior, lateral, or other approach.

In another embodiment, the distractor instrument may have a monorail on each lateral side to provide parallel alignment for instruments and implants having corresponding channels for insertion into the disc space.

In yet another embodiment, instrumentation for use in spinal surgery includes a distractor instrument with a recessed channel that receives a monorail on a lateral side of a surgical device or implant.

Various features and advantages of the present invention will become more apparent upon review of the detailed description set forth below when taken in conjunction with the accompanying drawings, which are briefly described as follows.

BRIEF DESCRIPTION OF THE DRAWINGS

FIG. 3 is a lateral view of the distractor of FIG. 1.

FIG. 4 is a side view of the distractor of FIG. 1.

FIG. 5 is a side view of a chisel according to one embodiment of this invention.

FIG. 6 is a perspective view of the chisel of FIG. 5.

FIG. 7 is a side view of a chisel and distractor assembly according to one embodiment of this invention.

FIG. 8 is a perspective view of a portion of the chisel and distractor assembly of FIG. 7.

FIG. 10 is a perspective view of a monorail instrument according to another embodiment of this invention.

FIG. 12 is a perspective view of the insertion tool of FIG. 11 and a guide according to one embodiment of this invention.

FIG. 13 is a perspective view of the assembly of an implant, distractor and insertion tool according to one embodiment of this invention.

FIGS. 17-18 are perspective views of alternative embodiments of this invention.

DETAILED DESCRIPTION

Figure 1:
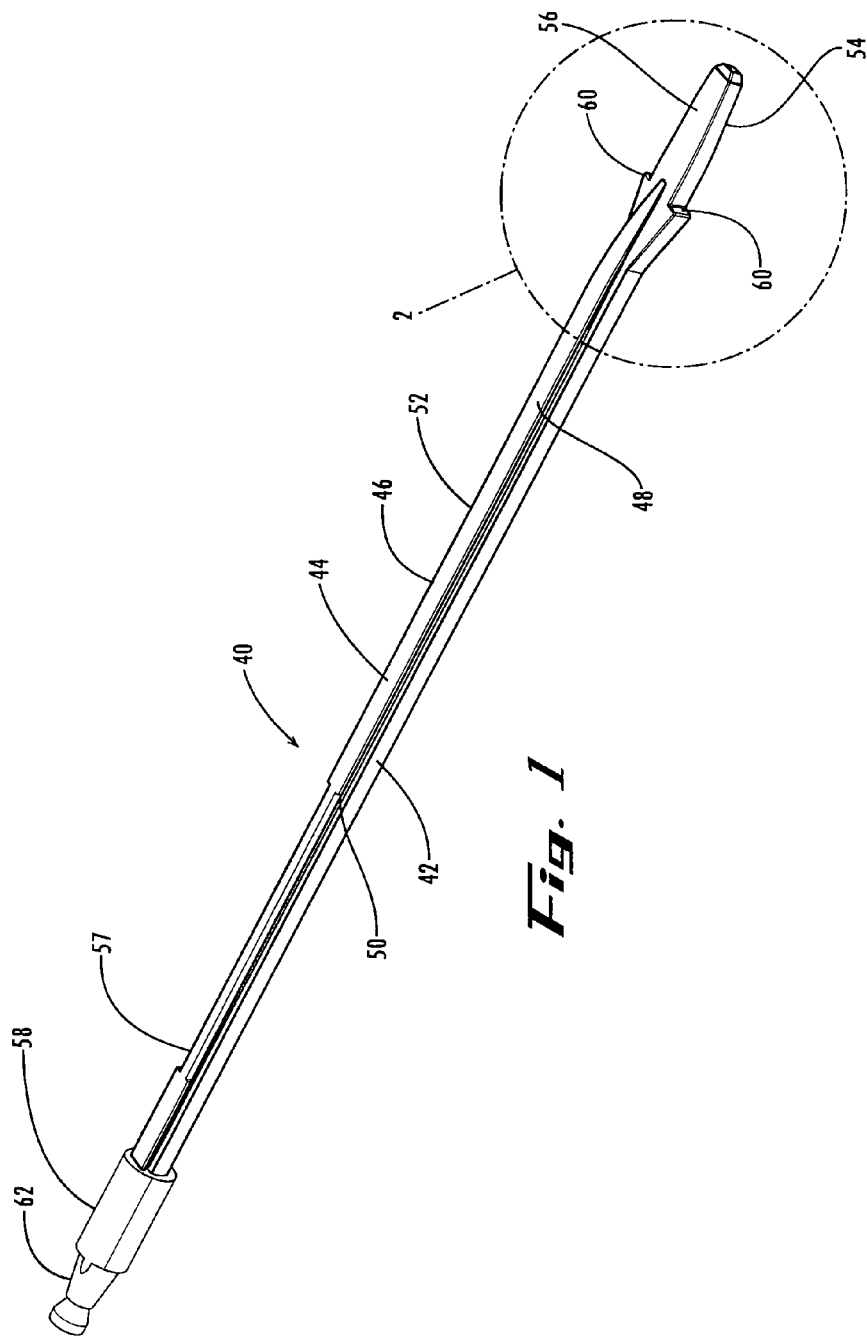
FIG. 1 is a perspective view of a monorail distractor according to one embodiment of this invention.
Figure 2:
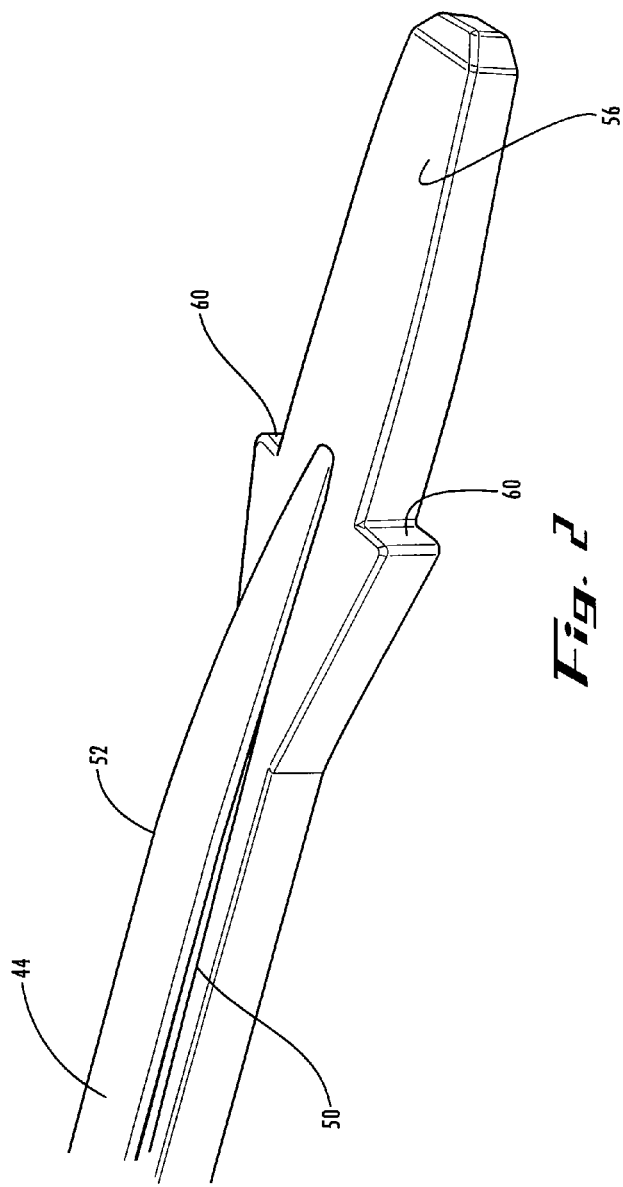
FIG. 2 is an enlarged perspective view of a portion of the distractor of FIG. 1.

The system of this invention provides an improved method of performing a spinal fusion procedure. Generally, the system includes a distractor instrument having a monorail on its lateral side that accommodates various other tools or instruments utilized to prepare the disc space. For example, additional instruments, such as a chisel, rasp, trial template and implant, may be designed with a recessed channel corresponding to the protruding monorail on a lateral side of the distractor instrument that assists in guiding and controlling the additional instruments and their use during a spinal fusion procedure. In certain exemplary embodiments, the distractor instrument may be inserted into the disc space and rotated to properly distract the disc space. The instrument may include additional monorails on any side so as to accommodate easy insertion and rotation without compromising a chosen approach medially or laterally. In other embodiments, an implant threaded to an insertion tool or other surgical instrument is inserted into the disc space using the monorail of the distractor instrument and the disc space is distracted relative to the size and dimensions of the implant.

Prior techniques have provided means for addressing the anterior spine by distracting above and below the disc space. The present invention, however, provides systems and methods for distracting the intervertebral disc space from inside the disc space and from side to side, facilitating proper spinal alignment, disc space reconstruction and allowing the implantation of a properly sized total disc replacement (TDR) device or fusion implant. During an anterior approach, one or more distractors may be used to aid in the reconstruction of the disc space for the TDR device. In an exemplary method of the present invention, a first distractor with a monorail is placed in or near midline of the disc space while a second distractor with a monorail is placed at the lateral edges of the disc space. A monorail may also be placed on the lateral edges of the disc space to allow an implant to slide between the two monorails which are acting as an insertion guide for the implant. A TDR device is attached to an insertion tool with the corresponding recessed channel to slide down the monorail of either the first or second distractor, insuring proper spinal alignment. In other embodiments of the present invention, one or more distractor instruments each having a single, recessed channel are inserted into the disc space. An insertion tool, implant, or other surgical instrument each having a monorail configured to engage the recessed channel of the distractor instrument is inserted into the disc space to distract, clean, and/or insert an TDR into the disc space. Those skilled in the art will readily appreciate other methods for approaching the intervertebral disc space using the systems and instruments described herein.

Reference will now be made in detail to various and alternative exemplary embodiments and to the accompanying drawings, with like numerals representing substantially identical structural elements. Each example is provided by way of explanation, and not as a limitation. It will be apparent to those skilled in the art that modifications and variations can be made without departing from the scope or spirit of the disclosure and claims. For instance, features illustrated or described as part of one embodiment may be used in connection with another embodiment to yield a still further embodiment. Thus, it is intended that the present disclosure includes modifications and variations as come within the scope of the appended claims and their equivalents.

Figure 25:
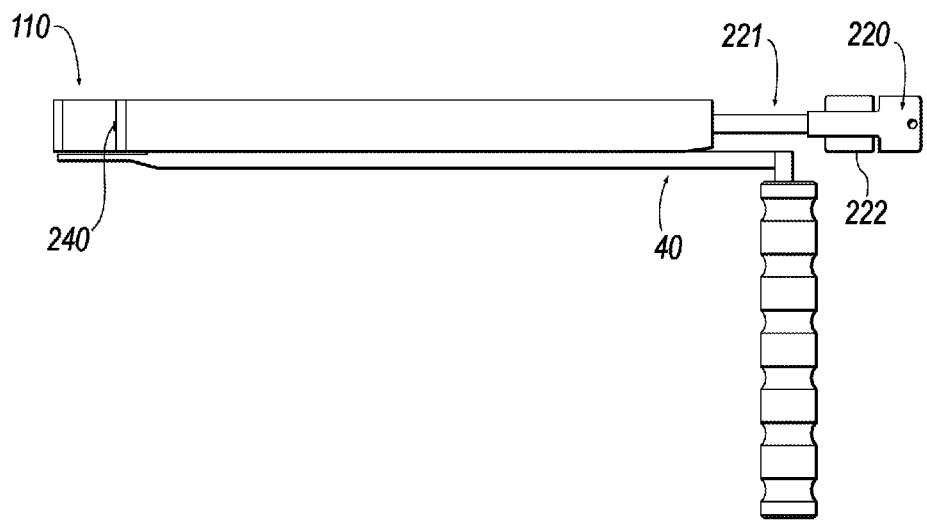
FIG. 25 is a side view of the distractor, insertion tool, and implant according to one embodiment of this invention.
Figure 26:
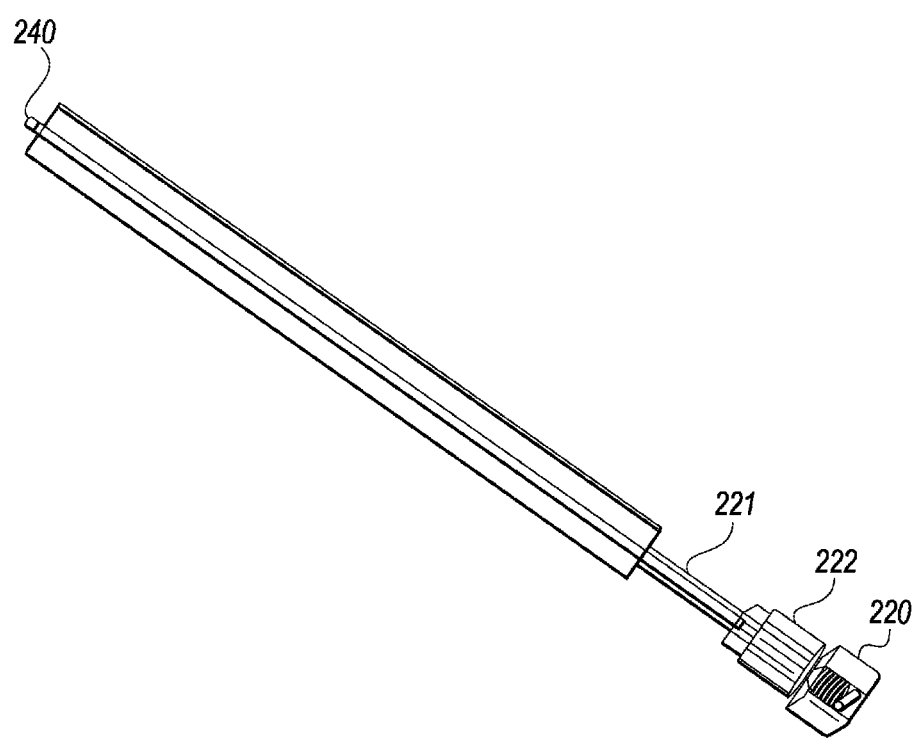
FIG. 26 is an exploded perspective view of the insertion tool of FIG. 21.

As shown in FIGS. 1-4, the monorail system of the present invention comprises a distractor 40, which includes a rod 42 having a monorail 44 on a lateral side 46. In accordance with the exemplary embodiments shown in the drawings, monorail 44 includes flat top portion 48 and angled sides 50, 52 (also shown in FIG. 9). The monorail 44 comprises an elongated member which protrudes from the lateral side 46 of the rod 42, forming a raised platform. Leading end 54 of the distractor 40 includes a tapered tip 56 for easy insertion into the disc space. In order to restore the disc height, a surgeon grasps a handle (not shown) attached to trailing end 58 and inserts leading end 54 of distractor 40 into the disc space. Shoulder 60 adjacent leading end 54 prevents distractor 40 from over extending into the disc space and damaging spinal tissue. In some embodiments, the distractor does no include shoulder 60. Once inserted into the disc space, the distractor 40 is then rotated 90 degrees to distract the disc space. In certain embodiments, the disc space is distracted via the insertion of an implant 110 or trial device into the disc space. In these embodiments, the amount of distraction of the disc space is relative to the dimensions of the implant 110 or trial device inserted into the disc space. Trailing end 58 of distractor 40 is configured to include a chuck 62 so that it may be joined to a handle, such as a Hudson handle (not shown). Any other suitable handle and handle engagement structure (an example of which is shown in FIG. 25) may also be used, as will be appreciated by those skilled in the art.

Once the proper distraction is achieved, the distractor 40 remains in the rotated position in the disc space in order to maintain proper distraction. A chisel, rasp, scraper or all three can then be used to clean and prepare the disc space for an implant, if desired.

Figure 9:
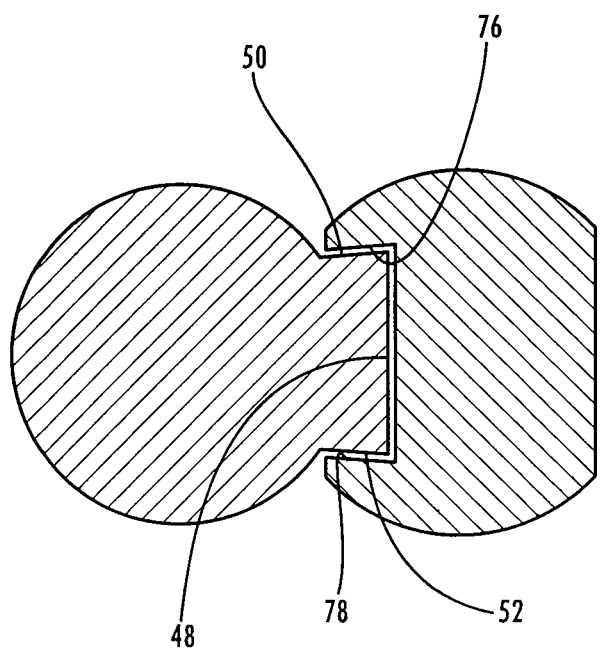
FIG. 9 is an end view in cross section of the chisel and distractor assembly of FIG. 7.

As shown in FIGS. 5-9, chisel 70 includes a channel 72, adapted to engage monorail 44 of distractor 40 (FIG. 9). The channel 72 includes a substantially flat inner surface 74 and slanted sides 76, 78 that correspond to the top portion 48 and angled sides 50, 52 of the monorail 44, respectively. The instruments are joined simply by engaging the leading end 80 of the channel 72 of chisel 70 with narrow section 57 of monorail 44 (shown in FIG. 1). In this manner, channel 72 of chisel 70 engages monorail 44 of distractor 40 so that chisel 70 slides down the rod 42 of distractor 40 and into the disc space. In alternative embodiments, the monorail and channel connection may include alternative structure, such as a rectilinear channel and rail, or any other suitable structure that joins the two instruments and allows controlled access to the disc space. For example, in certain embodiments the distractor instrument 40 may include a channel while the chisel 70 or other insertion tool may include a monorail that engages the channel of the distractor instrument.

As shown in FIG. 5, chisel 70 includes markings 82 or other indicia indicating depth of insertion. In an alternative embodiment, the rod 42 of monorail instrument 40 may include a stop to limit the insertion depth of the chisel into the disc space. The rod 42 shown in the drawings has a rectilinear shape, but any suitable shape, including circular, may be used.

Engagement of the chisel 70 (or other instrument) with the monorail 44 of the distractor instrument 40 thus provides guided delivery and access to the disc space. This controlled access protects the neural elements from potential injury from contact with instruments as they pass by or around the dura, nerve roots and other soft tissue. Once properly engaged with the monorail instrument, the chisel 70 may be impacted using a mallet (not shown) on handle 84 and extracted using a slaphammer (not shown) or any other suitable tool. Cutting end 86 of chisel 70 cuts away tissue, which may be captured in space 88 of chisel 70 and withdrawn from the disc space. A rongeur, or other suitable instrument, may also be used to extract the separated tissue.

In an alternative embodiment, a monorail device may be equipped to prepare the disc space without the use of a chisel or rasp, or in addition to such instrumentation. In this alternative embodiment shown in FIG. 10, the edges 90 of the leading end 92 of the distractor instrument 40 include flutes 96, equipping the monorail device with the ability to cut away soft tissue in the disc space and off the vertebral endplates. In this embodiment, the leading end 92 is inserted into the disc space and rotated to distract the space. Rotating the distractor instrument 40 causes flutes 96 to cut away tissue. The distractor instrument 40 may be rotated back and forth to remove the tissue. A rongeur may be used to extract the separated tissue. A chisel, rasp, or other appropriate instrument may also be used (as described above) if additional preparation of the disc space is required.

Figure 14:
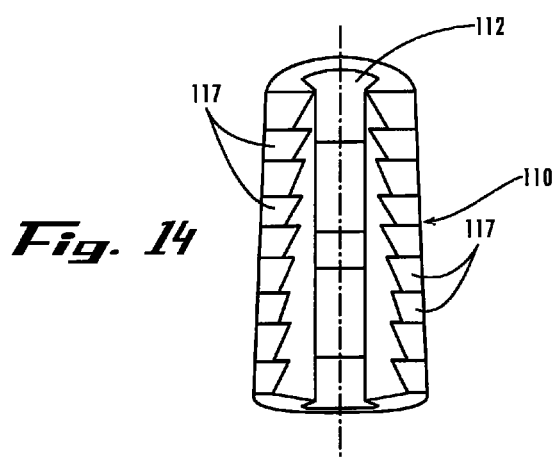
FIGS. 14-16 are alternative side views of an implant of this invention.
Figures 15, 16:
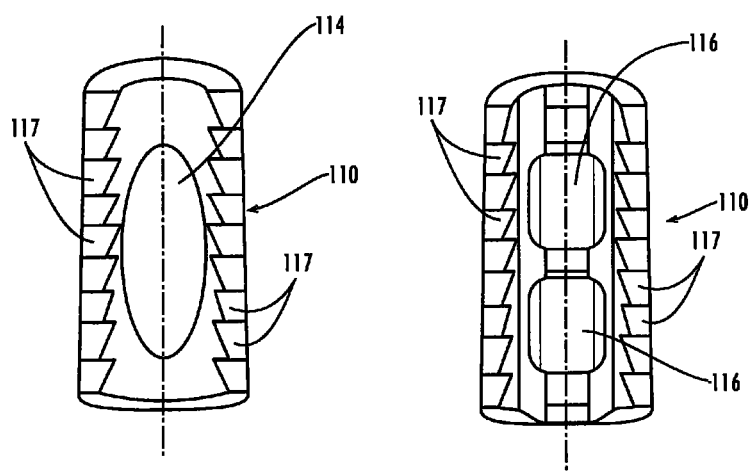
Figure 11:
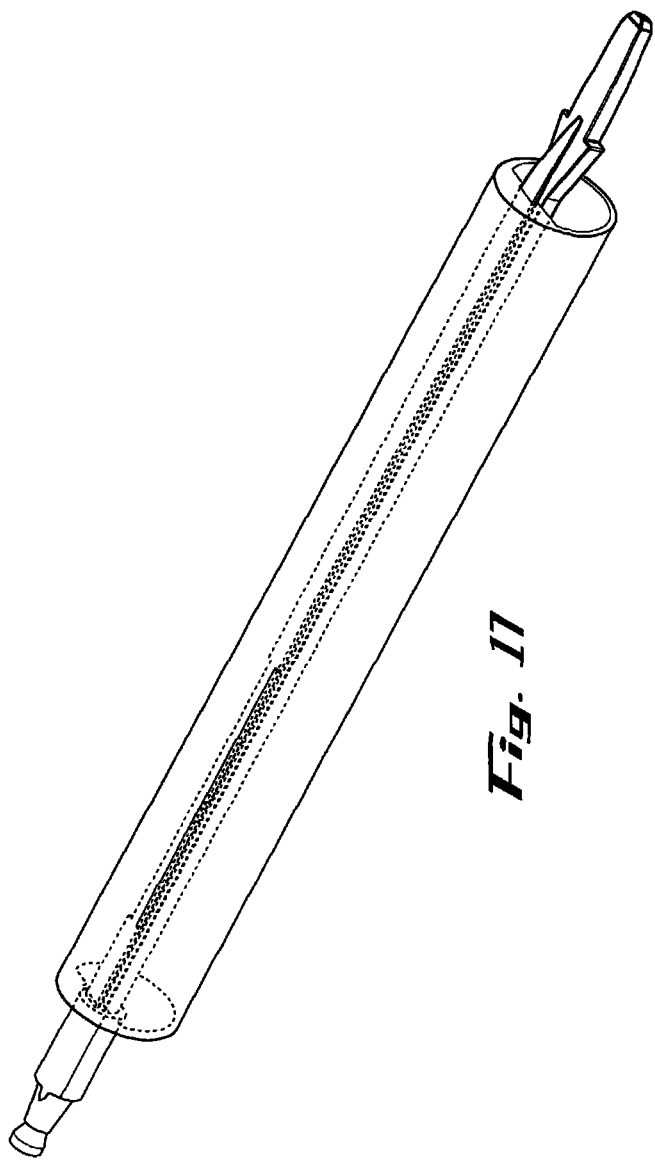
FIG. 11 is a side view of an insertion tool according to one embodiment of this invention.

Once the disc space is prepared and ready for fusion, an inserter, exemplary embodiments of which are shown in FIGS. 11 and 12, may be used to place an implant 110, examples of which are shown in FIGS. 14-16, into the disc space. Inserter 100 includes threads 102 on leading end 104, which engage a corresponding threaded aperture 106 (not shown) on implant 110. The implant 110 includes channel 112, shown in FIG. 14 and similar to channel 72 of chisel 70 described above. Channel 112 of implant 110 engages monorail 44 of distractor 40 so that inserter 100 and implant 110 slide down distractor 40 and into the disc space. In one embodiment, a guide 111, shown in FIG. 12, may be used to maintain the engagement of the inserter 100 with the monorail 44.

In an alternative embodiment, the implant 110 has a monorail similar to monorail 44 of the distractor 40 described above and the distractor 40 includes a channel similar to channel 72 of the chisel 70 described above. In this embodiment, the implant 110 is able to slide longitudinally relative to the distractor by engaging the channel of the distractor 40 with the monorail of the implant 110. In yet another alternative embodiment, the inserter 100 has a monorail similar to monorail 44 of the distractor 40 described above and the distractor 40 includes a channel similar to channel 72 of the chisel 70 described above. In this alternative embodiment, the inserter 100 is able to slide longitudinally relative to the distractor by engaging the channel of the distractor 40 with the monorail of the inserter 100. These alternative embodiments may include without limitation the use of the implant 110 threaded to the inserter 100 or the use of the implant 110 or the inserter 100 separately from one another.

Once implanted, openings on implant 110, such as oval apertures 114 and additional apertures 116, shown in FIGS. 15-16, respectively, allow bone to grow through the implant and stabilize the fusion of the two vertebrae. As shown in the drawings, the channel 112 of the implant 110 is located on the inner wall of the implant 110. Two implants can thereby be nested together to provide a better anatomical fit to the interbody space and reduce the chance of neural injury to the lateral or descending nerve roots. The implant has raised teeth 117 to help prevent retropulsion once delivered to the disc space.

As discussed above, in alternative embodiments, a delivery system according to certain embodiments of the invention includes a distractor having a channel for accepting a monorail. In these embodiments, the implant, inserter, or other surgical instrument may include a monorail to engage the channel of the distractor. Additional instrumentation, such as a chisel and a rasp, may also be designed to include a monorail, so that these instruments engage the channel of the distractor.

Figure 18:
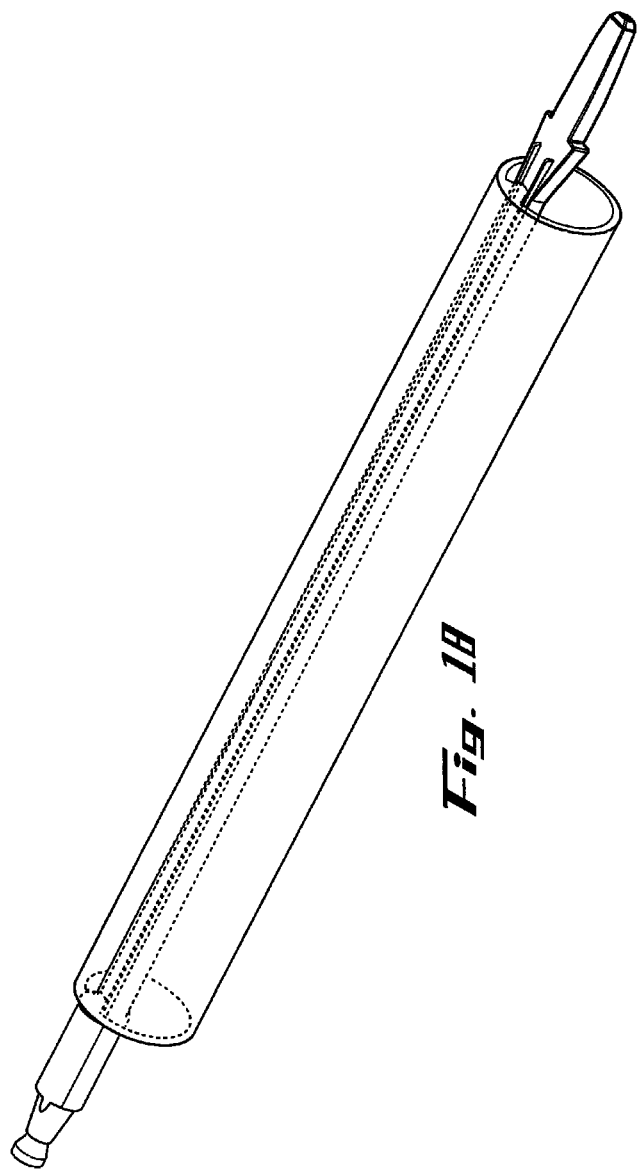

Embodiments of this invention may be used with standard instrumentation, as well as through a channel or circular delivery system that is introduced by a collapsed tubular retractor that is inserted into the surgical site and dilated. In one embodiment, shown in FIG. 17, a tubular retractor includes a monorail, so that an implant having a channel engages the monorail and slides down the tubular retractor into the disc space. In another embodiment, shown in FIG. 18, the tubular retractor includes a channel adapted to engage a monorail, so that an implant having a monorail engages the channel and slides down the tubular retractor into the disc space.

The monorail distractor 40 of this invention may be made in various sizes to accommodate different patient anatomies. In one embodiment, a 7 mm distractor is used. In other embodiments, the monorail instrument is a 9, 11 or 13 mm distractor, or any other suitable size.

Figure 19:
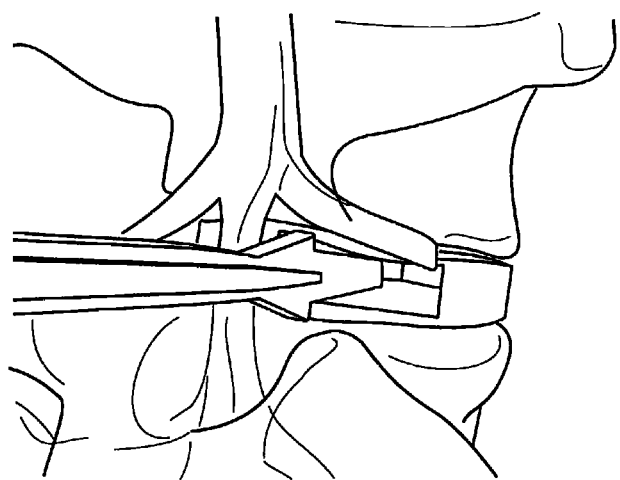
FIG. 19 illustrates placement of a monorail instrument of this invention into the intervertebral space.
Figure 20:
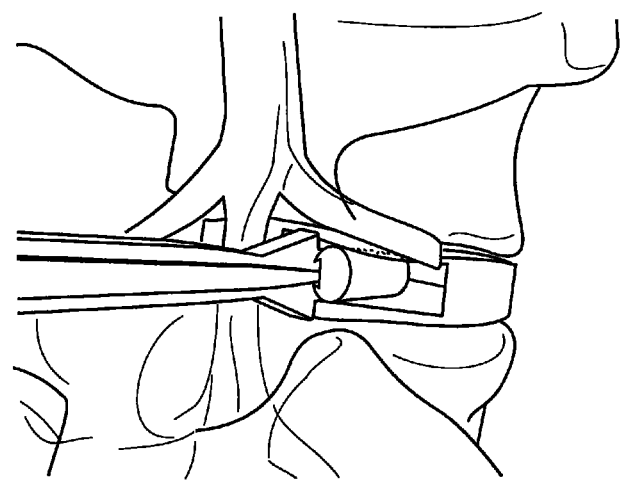
FIG. 20 illustrates placement of an implant of this invention into the intervertebral disc space.

FIGS. 19-20 illustrate placement of a monorail distractor (FIG. 19) and an implant (FIG. 20) according to certain exemplary embodiments of this invention. In one embodiment, as shown in FIG. 19, the monorail instrument is inserted into the disc space and rotated 90° to distract the intervertebral disc space. Then, an implant device having a recessed channel engages and slides down the monorail and into the disc space, as shown in FIG. 20.

Figure 21:
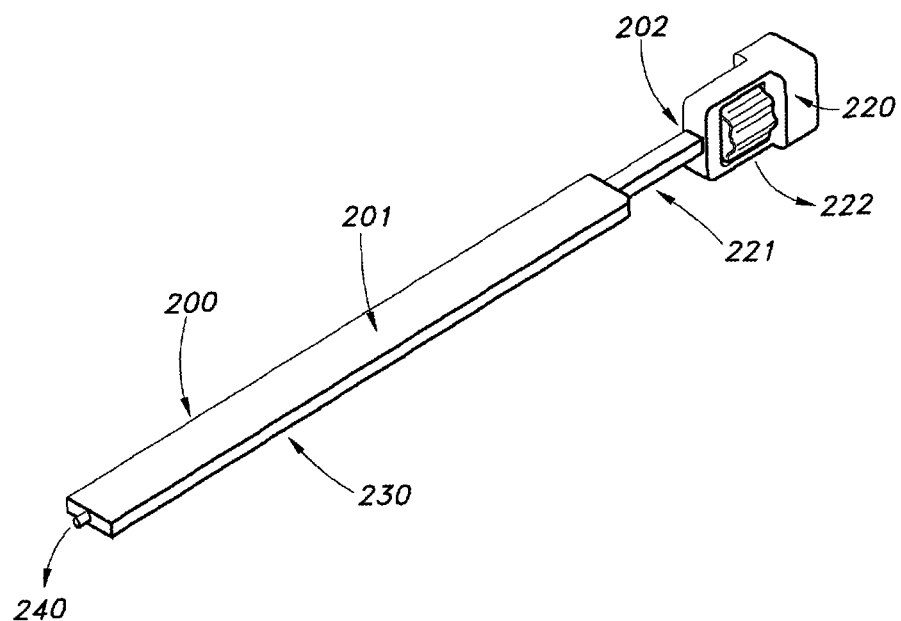
FIG. 21 is a perspective view of an insertion tool according to another embodiment of this invention.

FIG. 21 illustrates an alternative embodiment of an inserter for inserting an implant according to this invention. The inserter 200 includes a distal portion 201 and a proximal portion 202. The proximal portion 202 includes a housing 220 located adjacent a shaft 221. Housing 220 can serve as an impaction cap when the surgeon needs to use a mallet, or other suitable device, to propel the inserter 200 forward along the monorail. Also, housing 220 has a pin and spring inside of it so a slap hammer can be attached should the implant need to be retrieved from the disc space.

Figure 24:
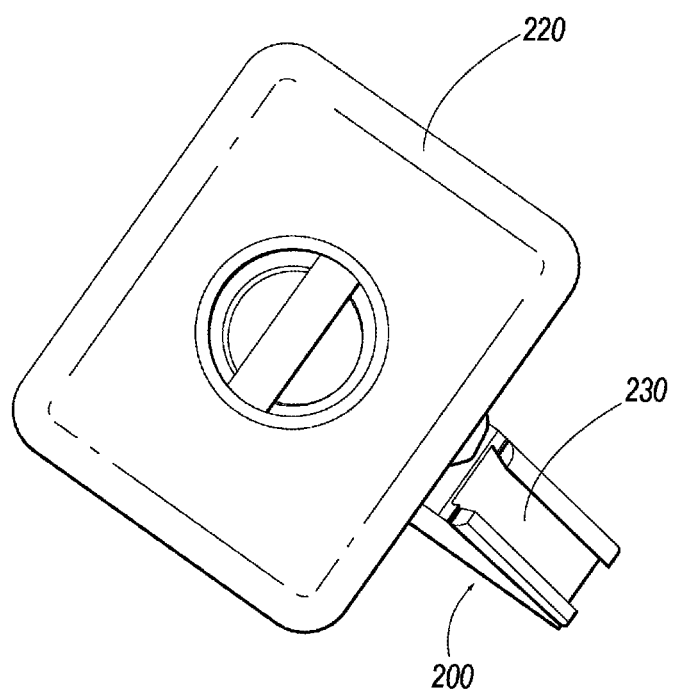
FIG. 24 is a second end view of the insertion tool of FIG. 21.

A bore (not shown) runs through the inserter 200, extending from an aperture 225 at the leading end 226 of the distal portion 201 and through the shaft 221. A rod 210 housed within the bore includes a distal end 240, which protrudes past the leading end 226 of the distal portion 201, as shown in FIG. 21. The distal end 240 of the rod 210 includes a threaded portion 212. A threaded knob 222, in opening 223 of housing 220, is operably connected to the proximal end (not shown) of rod 210 such that the movement of the knob 222 controls movement of the rod 210. A channel 230 (shown in FIG. 24), similar to the channel 72 of the chisel 70, is located on a lateral side of the distal portion 201 of the inserter 200.

Figure 22:
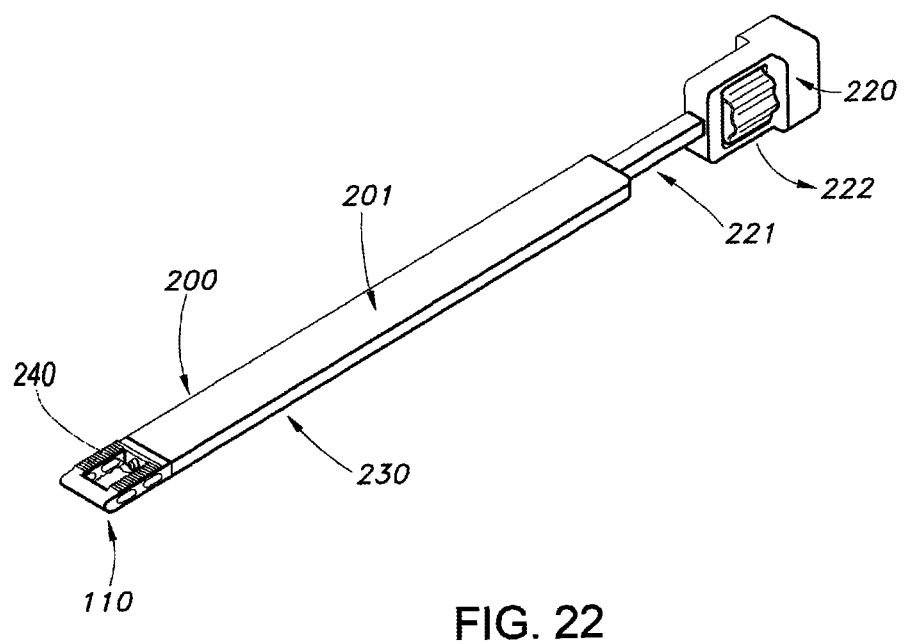
FIG. 22 is a perspective view of the insertion tool of FIG. 21 and an implant according to one embodiment of this invention.

In one embodiment, the threaded portion 212 of the distal end 240 of rod 210 engages the threaded aperture 106 of implant 110, as shown in FIG. 22. The channel 230 engages the monorail 44 of distractor such that the inserter 200 is able to move along the monorail 44 in a longitudinal direction but is prevented from disengaging the monorail laterally.

Figure 23:
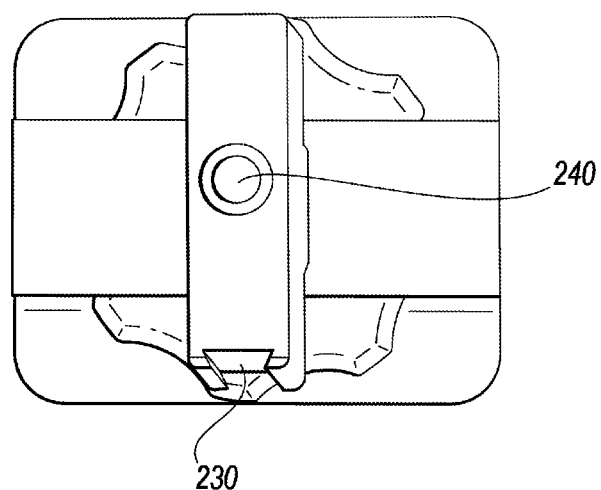
FIG. 23 is a first end view of the insertion tool of FIG. 21.

Embodiments of the total disc replacement system of the present invention may be used in various methods of delivering instruments and implants to the intervertebral spinal cavity. The tools and components discussed in FIGS. 21-23 are referenced herein for purposes of illustration only. In one method of the present invention, the monorail 44 of the distractor 40 is inserted into the disc space from a posterior approach and rotated 90° to distract the disc space. An implant 110 is threaded to distal end 240 of rod 210 of inserter 200 by turning the threaded knob 222 in a first direction. The channel 230 of the inserter 200 is engaged with monorail 44, as is shown in FIG. 25. Upon proper distraction, the inserter 200 is advanced down the distractor 40 in sliding engagement with the monorail 44, guiding the implant 110 into the space created by the distraction. This ensures proper size and placement of the implant so it does not need to be oversized or undersized. In another embodiment, rather than rotating the distractor to distract the disc space, the disc space is distracted via the insertion of a trial attached to an inserter and engaged to the monorail distractor. When the proper disc height is attained, the trial and insertion tool are removed leaving the monorail distractor in the disc space. The monorail distractor keeps the disc space open, thus allowing for proper cleaning and preparation for fusion. Once prepared, implant 110 will be attached to the inserter tool which is engaged onto the monorail and slid into the disc space using the unique monorail design of the present invention. In this embodiment, the distraction is directly proportional to the size and dimension of the inserted trial or implant.

The systems of this invention may be used in a variety of disc replacement procedures and from different approaches and forms. The tools and instruments described above may be used in total disc replacement (TDR) procedures. These systems may be used to deliver a single TDR device or multiple surgical components, such as an inserter, a disc preparation instrument (e.g. a chisel), or other instrumentation. In one exemplary method using the systems of this invention, a TDR device is inserted into the intervertebral disc space using a monorail instrument, which has properly distracted the disc space in accordance with the 90° rotation described above. An inserter is coupled to the TDR device and slides onto the monorail and into the disc space for placement. In another exemplary method, two distractors, each with a monorail, may be utilized when delivering implants, with each distractor inserted into the disc space from either sides of the disc space. This allows one monorail device to serve as a distractor on one side while the other monorail device is used to deliver surgical instruments and the implant into the disc space.

Alternatively, in situations in which multiple implants are to be inserted into different portions of the disc space, a distractor with a monorail on each lateral side may be utilized to insert the implant devices in parallel alignment and equidistant from one another. Thus, if the instrument is inserted in such a way that the first monorail is facing lateral, a second monorail on the opposing side would allow placement of an implant on the medial side and vice versa. In yet another exemplary method, a single distractor with a monorail may be inserted in the disc space at midline, providing equal distraction across the disc space.

As discussed above, the systems of the invention may be used in a variety of surgical approaches. If a direct lateral approach to the spine is used for a TDR device or fusion implant, any of the systems discussed above provide for an excellent means of reconstructing the disc space. The systems and methods of the present invention greatly reduce the difficulties associated with a lateral approach. The need to under or over size an implant as well as struggling with the distraction process from the lateral incision approach is eliminated by embodiments of the present invention. One or more distractors can be placed in the disc space through a lateral approach. Both posterior and anterior distractors can be placed to achieve proper spine alignment during reconstruction of the disc space Alternatively, a lateral distractor can be placed in conjunction with either a posterior or an anterior distractor.

The tools and instruments described above provide many advantages over prior art systems. For example, some existing distractor systems require assembly in the disc space and are comprised of multiple pieces, which can lead to more complications arising during the surgical procedure. Adding further difficulty, if an improperly sized device is chosen in existing systems, displacement of the device or parts of the device may occur. Based on the foregoing, it can be seen that the present invention provides improved systems and methods of performing a spinal fusion procedure that include a monorail instrument having a sliding platform to allow controlled delivery of various instruments for disc preparation and implant insertion in order to protect the medial neural structures of the spine.

Many other modifications, features and embodiments of the present invention will become evident to those of skill in the art. For example, those skilled in the art will recognize that embodiments of the present invention are useful and applicable to a variety of spinal fusion procedures, including, but not limited to, ALIF, PLIF, TLIF, and XLIF procedures (or lateral procedures).

Accordingly, it should be understood that the foregoing relates only to certain embodiments of the invention, and are presented by way of example rather than limitation. Numerous changes may be made to the exemplary embodiments described herein without departing from the spirit and scope of the invention as defined by the following claims.

The invention claimed is:

1. A system for delivering surgical devices to a spinal column of a patient, comprising:
   (a) a distractor instrument comprising a monorail on a lateral side, wherein the monorail comprises a single raised platform and two sides angled inwardly from the raised platform, and wherein the monorail extends substantially along a length of the distractor instrument, wherein rotation of the distractor instrument is configured to distract a disc space;
   (b) an inserter instrument, comprising:
      a first portion having a recessed channel along at least one lateral side for receiving the raised platform of the monorail, wherein the recessed channel engages the raised platform of the monorail to permit longitudinal movement between the distractor instrument and the inserter instrument and wherein once engaged, the distractor instrument and the inserter instrument cannot be disengaged laterally, the inserter instrument positionable in the distracted disc space after rotation of the distractor instrument;
      a second portion including a shaft and a housing, wherein a threaded knob is disposed within the housing;

a rod disposed in the first portion and the second portion, wherein the rod comprises a threaded end protruding from a leading end of the inserter and is attached to the threaded knob so that the threaded knob controls circumferential movement of the rod; and (c) a total disc replacement device comprising an opening for receiving the threaded end of the rod.

2. The system of claim 1, wherein the distractor instrument further comprises a second lateral side having a single elongated member.

3. The system of claim 1, wherein the distractor instrument further comprises at least one shoulder adjacent a leading end for limiting a distance at which the distractor instrument is inserted into the disc space.

4. The system of claim 3, wherein the leading end of the distractor instrument comprises flutes for cutting away tissue.

5. The system of claim 1, wherein the distractor instrument further comprises a handle.

6. The system of claim 1, wherein the total disc replacement device is an implant.

7. The system of claim 6, wherein the implant comprises a recessed channel along at least one lateral side for receiving the raised platform of the monorail, wherein the recessed channel of the implant engages the raised platform of the monorail to permit longitudinal movement between the distractor instrument and the implant and wherein once engaged, the distractor instrument and the implant cannot be disengaged laterally.

8. The system of claim 1, further comprising at least one surgical instrument.

9. The system of claim 8, wherein the at least one surgical instrument comprises a recessed channel along at least one lateral side for receiving the raised platform of the monorail, wherein the recessed channel of the at least one surgical instrument engages the raised platform of the monorail to permit longitudinal movement between the distractor instrument and the surgical instrument and wherein once engaged, the distractor instrument and the surgical instrument cannot be disengaged laterally.

10. The system of claim 9, wherein the at least one surgical instrument is a chisel.

11. A method of performing spinal fusion surgery, comprising:

(a) inserting a distractor into a disc space, wherein the distractor comprises a monorail on at least one lateral side;

(b) distracting the disc space by rotating the distractor in a first direction;

(c) coupling a total disc replacement device to a threaded rod of an inserter by turning a threaded knob of the inserter in a first circumferential direction, the total disc replacement device having a channel for receiving the monorail of the distractor;

(d) engaging a recessed channel of the inserter and the recessed channel of the total disc replacement device with the monorail of the distractor;

(e) sliding the inserter and total disc replacement device longitudinally down the monorail and into the distracted disc space;

(f) decoupling the total disc replacement device from the inserter by turning the threaded knob in a second circumferential direction; and (g) removing the inserter and distractor from the disc space.

12. The method of claim 11, wherein the distractor is inserted into the disc space from an anterior approach.

13. The method of claim 11, wherein the distractor is inserted into the disc space from a posterior approach.

14. The method of claim 11, wherein the distractor is inserted into the disc space from a transforaminal approach.

15. The method of claim 11, wherein the distractor is inserted into the disc space from an extreme lateral approach.

16. The method of claim 11, wherein a first distractor including a monorail is inserted from a lateral approach on a first side of the disc space and a second distractor including a monorail is inserted from a lateral approach on a second side of the disc space.

17. The method of claim 11, wherein the step of distracting the disc space is performed prior to the step of sliding the inserter and total disc replacement device.

18. The method of claim 11, wherein the monorail is disposed on an exterior surface of the distractor.

19. A method of performing spinal surgery comprising:
inserting a distractor into a disc space between adjacent vertebral bodies, the distractor having a monorail extending laterally from one side thereof;
rotating the distractor in a first direction, thereby distracting the disc space;
providing an inserter, the inserter having a recess that is complementary to the monorail and a rod with a threaded end;
coupling a disc replacement to the threaded end of the rod, the disc replacement having a channel for receiving the monorail of the distractor;
engaging the inserter and the disc replacement to the distractor by sliding the inserter and the disc replacement longitudinally along the monorail;
positioning the disc replacement in the distracted disc space;
separating the disc replacement from the inserter; and
removing the inserter and the distractor from the distracted disc space.

20. The method of claim 19, wherein once the inserter and the distractor are engaged, the inserter and the distractor are laterally fixed to one another.

* * * * *